United States Patent
Kondo et al.

(10) Patent No.: US 6,268,512 B1
(45) Date of Patent: Jul. 31, 2001

(54) PROCESS FOR PRODUCING 3-METHYL-2-OXOINDOLINE

(75) Inventors: Hisao Kondo, Kanagawa; Tetsuro Higashikawa, Tokyo, both of (JP)

(73) Assignee: Medical Information Services, Inc., Tokyo (JP)

( * ) Notice: Subject to any disclaimer, the term of this patent is extended or adjusted under 35 U.S.C. 154(b) by 0 days.

(21) Appl. No.: 09/600,019

(22) PCT Filed: Jan. 8, 1999

(86) PCT No.: PCT/JP99/00026

§ 371 Date: Jul. 11, 2000

§ 102(e) Date: Jul. 11, 2000

(87) PCT Pub. No.: WO99/36401

PCT Pub. Date: Jul. 22, 1999

(30) Foreign Application Priority Data

Jan. 16, 1998 (JP) .................................................. 10-006806

(51) Int. Cl.$^7$ ................................................. C07D 207/12
(52) U.S. Cl. ............................................................ 548/543
(58) Field of Search ............................................. 548/543

(56) References Cited

FOREIGN PATENT DOCUMENTS

| 45-28982 | 9/1970 | (JP) . |
| 1-110681 | 4/1989 | (JP) . |

OTHER PUBLICATIONS

"3H–Indole no kenkyuu (I) Oxindole, Indole o heru 3, 3–jichikan 3H–Indole no shin gouseihou", by Isobe et al., Journal of the Pharmaceutical Society of Japan, vol. 94, No. 3, 1974, pp. 343–350.

"Synthesis of 1,3–Dihydro–3, 3–dimethyl–2H–indol–2–one Derivatives as Possible Nonsteroidal Cardiotonics", by Lee et al., J. Heterocycl. Chem., vol. 32, No.1, 1995, pp. 1–11.

*Primary Examiner*—Joseph K. McKane
*Assistant Examiner*—Ebenezer Sackey
(74) *Attorney, Agent, or Firm*—McDermott, Will & Emery

(57) ABSTRACT

The present invention is a process for producing 3-methyl-2-oxoindoline as defined by the following chemical formula (2), including heating of propionylphenylhydrazide as defined by the following chemical formula (1) in the presence of at least one kind of basic calcium compound, characterized in that an organic solvent withstanding at least at a temperature of 180° C. in the presence of the basic calcium compound is employed by at least an amount of equal weight to that of the propionylphenylhydrazide. With the construction mentioned above, even when the amount of calcium oxide is reduced down to as little as 15% of a conventionally used amount, at least 75% of a corresponding yield attained conventionally has been achieved. That is, not only control of the reaction and easy after treatment but also a high yield has been achieved;

2 Claims, 1 Drawing Sheet

PROCESS FOR PRODUCING 3-METHYL-2-OXOINDOLINE

TECHNICAL FIELD

The present invention relates to a process for producing 3-methyl-2-oxoindoline, which is a chemical intermediate for producing various fine chemicals including ketoprofen (chemical name: 2-(3-benzoylphenyl) propionic acid) which is known as an anti-inflammatory agent.

BACKGROUND ART

Various conventional processes for producing 3-methyl-2-oxoindoline (chemical formula (2)) have hitherto been proposed, typical examples of which are as follows:

(A) reduction of α-(2-nitrophenyl) propionic acid (Ann., 227, 274 (1885)).

(2)

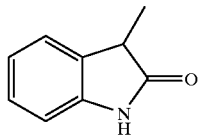

(B) heating of propionylphenylhydrazide (chemical formula (1)) using; calcium oxide (Monatsh., 18, 533 (1897)).

(1)

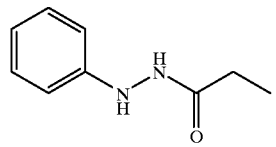

(C) heating of propionylphenylhydrazide using calcium hydride (Org. Syn., Coll. Vol., IV, 657).
(D) oxidation of skatole using persulfuric acid (J. Chem. Soc., 1958, 3726).
(E) heating of 2-chloropropionylanilide, which is produced by condensating aniline and 2-chloropropionyl chloride, in the presence of aluminum chloride (Tetrahededoron, 24, 6093 (1968), J. Med., Chem., 25, 446 (1970)).
(F) reaction of o-nitrotoluene to produce 2-(2-nitrophenyl) 1,3-propanediol by using formaldehyde in the presence of base, followed by oxidation thereof to produce 2-(2-nitrophenyl) propenal by dehydration using dimethylsulfoxide-dicyclohexylcarbodiimide, reaction thereof to produce epoxide using hydrogen peroxide, and reduction by hydrogenation (Bull. Chem. Soc., 62, 4061 (1989).

However, the process (A), in which the starting material has not been produced by an industrial process, needs numbers of steps and is not practical.

Although the process (B) is simple and excellent, a large amount of calcium oxide (secondary raw material) that is about four times as much as the main raw material in weight and that about ten times in molar ratio is consumed to advance the reaction. Therefore, as for after treatment of the reaction, since water addition accompanying heat generation and neutralization using a large amount of hydrochloric acid are necessary in order to treat the residual calcium oxide, it is very hard to implement iron an industrial scale.

In the process (C), calcium hydride is used instead of calcium oxide used in the process (B). However, calcium hydride is an expensive reagent, and the control of reaction is difficult since a rapid reaction takes place upon heating, and the after treatment of neutralizing excess calcium hydride is very difficult to implement, therefore the practice according to the process (C) in an industrial scale is very hard to implement.

In the process (D), the starting material, i.e. skatole is expensive, and the process does not result in an inexpensive process.

A supplementary test of the process (E) has revealed a generation of structural isomer, i.e. 2-oxazolinone (chemical formula (3)), separation of which is difficult even in its recrystallization refining. 2-oxazolinone has the same molecular formula and a similar structure with 3-methyl-2-oxoindoline, i.e. an objective chemical, and its separation by normal refining method such as recrystallization method is difficult to implement, therefore the process (E) is not practical.

(3)

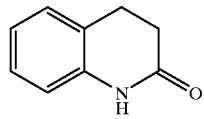

The process (F) includes many steps and uses expensive reagents, therefore it is very hard to implement in an industrial scale.

Although 3-methyl-2-oxoindoline is a chemical intermediate (Japanese Patent Application No. H9-111236) for producing ketoprofen that has been proposed by the present inventors and is expected as a chemical intermediate for producing various fine chemicals from the viewpoint of its stricture, its producing process in an industrial scale has not yet been established.

The present inventors have already proposed an efficient process for producing ketoprofen (Japanese Patent Application No. H9-111236), in which 3-methyl-2-oxoindoline (chemical formula (2)) is benzoylated to be 5-benzoyl-3-methyl-2-oxoindoline, then an amide bond in a five-membered ring of which is cleavaged using a basic compound and then, a generated aromatic amino group is replaced by a hydrogen atom. An example of the reaction is shown in a chemical formula (4) as follows:

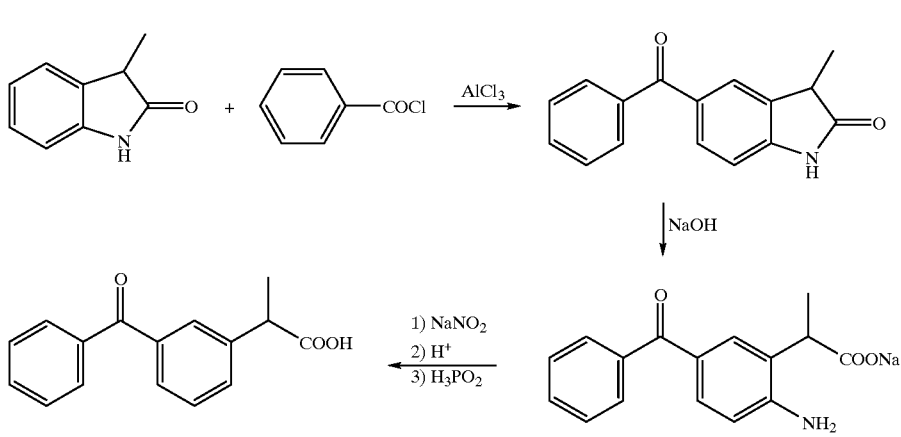

The above mentioned process (B) for producing 3-methyl-2-oxoindoline is an excellent process because inexpensive starting, materials are used, however according to the reference, a large amount of calcium oxide that is about four times as much as the main raw material of propionylphenylhydrazine in weight is used and therefore, its after treatment of the reaction is very difficult (see the following comparative example No. 1). A study has revealed that reducing the necessary amount of calcium oxide results in marked decrease in the yield (see the following comparative examples No. 2 and 3).

In addition, a further study has revealed that a certain amount of calcium oxide makes the reaction advance rapidly, therefore, the temperature control becomes difficult to implement (see the following comparative examples No. 4).

The present inventors have studied to solve the two problems mentioned above and reached the present invention in which an organic solvent such as tetrahn, which can stand at reaction temperature 190 to 230° C., can be employed so as to solve the problems.

It is therefore an objective of the present invention to provide an efficient process for producing 3-methyl-2-oxoindoline that is a key chemical intermediate for producing ketoprofen efficiently.

DISCLOSURE OF INVENTION

In order to attain the above objective, the present invention is to provide a process for producing 3-methyl-2-oxoindoline as defined by the following chemical formula (2), comprising heating of propionylphenylhydrazide as defined by the following chemical formula (1) in the presence of at least one kind of basic calcium compound, characterized in that an organic solvent withstanding at least at a temperature of 180° C. in the presence of the basic calcium compound is employed by at least an amount of equal weight to that of the propionylphenylhydrazide.

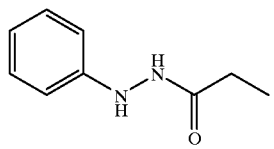

(1)

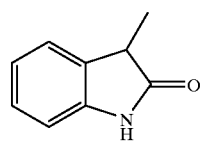

(2)

With the construction of the present invention mentioned above and as apparent from the following Examples, even when the amount of calcium oxide is reduced down to as little as 15% of a conventionally used amount, at least 75% of a corresponding yield attained conventionally has been achieved. That is, not only control of the reaction and easy after treatment but also a high yield has been achieved.

The starting material of the present invention, i.e. propionylphenylhydrazide (chemical formula (1)) can be easily synthesized with a high yield by a reaction between commercially available phenylhydrazine and anhydrous propionic acid.

As the secondary raw material of the present invention, basic calcium compounds such as calcium oxide, calcium carbide, calcium hydride and calcium alkoxide are suitably used. When calcium hydroxide or calcium carbonate is used, no reaction takes place or no desirable result is attained From the viewpoints of the economy and easiness of the after treatment after the reaction, calcium oxide is most preferably used. In addition, a reactant system that can generate a basic calcium compound, for example, a reactant system consisting of calcium chloride, sodium hydride and sodium methoxide, is also included in the secondary raw material of the present invention.

The organic solvent withstanding at least at a temperature of 180° C. in the presence of the basic calcium compound is preferably a hydrocarbon having aromaticity such as tetralin and diisopropyl benzene, unsaturated hydrocarbon such as 1,5,9-cyclododecatriene, various amines such as xylidine, ethylaniline, diethylaniline, tributylamine, quinoline and 1,8-diazabicyclo[5,4,0]-7-undecene, ethers such as diphenyl ether, butylphenyl ether, hexyl ether and diethylene glycol dibutyl ether, and hydrocarbon containing halogen such as 1,2,4-trichlorobenzene, but the organic solvent is not limited to the above examples. Above all, tetralin is most preferably used since tetralin is inexpensive and easy to handle.

The organic solvent withstanding at least at a temperature of 180° C. in the presence of basic calcium compound described in the present invention is not limited to an organic solvent having a boiling point or decomposition temperature being at least 180° C., but includes an organic solvent having a boiling point or decomposition temperature being at least 180° C. under a pressurized environment in the presence of calcium compound provided that the organic solvent is used in such a pressurized environment.

In the process for producing 3-methyl-2-oxoindoline according to the present invention, the reaction must be carried out at least at a temperature of 180° C. At a temperature below 180° C., the reaction does not take place or proceeds significantly slowly, therefore the reaction cannot be carried out efficiently.

The using amount of basic calcium compound is 0.2 to 2 times as much as the main raw material of propionylphenylhydrazide in weight and preferably 0.5 to 1.0 times. When the using amount is less than 0.2 times as much as the main raw material in weight, the reaction proceeds slowly and the reaction yield deteriorates. When the using amount is more than 2 times as much as the main raw material in weight, unreacted basic calcium compound remains, then a time consuming and costly after treatment thereof becomes needed.

The using amount of the organic solvent withstanding at least at a temperature of 180° C. in the presence of basic calcium compound is 1 to 20 times as much as the main raw material of propionylphenylhydrazide in weight and preferably 3 to 10 times. When the using amount is less than 1 times as much as the main raw material in weight, the reaction yield and control of the reaction become insufficient. Even when the using amount is more than 20 times as much as the main raw material in weight, further improvement in a yield is hardly attained.

BEST MODE FOR CARRING OUT THE INVENTION

In the following, the present invention is explained with reference to examples, however, by no means limited to the examples. On the other hand, prior art is explained with reference to comparative examples.

Comparative Example 1 (Synthesis on the Basis of the Conventional Process (B))

In an inert gas (Ar gas) atmosphere, a reaction between propionylphenylhydrazide (10.0 g, 0.061 mol) and commercially available calcium oxide powder (40.0 g, 0.714 mol) was advanced under agitation with raising temperature gradually from 200° C. to 230° C. The progress of the reaction was checked on the basis of generation of ammonia gas.

After confirming the end of the ammonia gas generation, the reaction system was cooled down to room temperature, then water (150 ml) was added gradually thereinto under cooling with ice. At that time, the reaction advanced violently with generating heat. After the addition of water, ethyl acetate (150 ml) was added thereinto and then, commercially available concentrated hydrochloric acid (120 ml) was dropped gradually thereinto to neutralize the system. After the end of dissolution of the solid component, the separated organic layer was washed twice with water. The system was dried by using anhydrous magnesium sulfate and separated by filtration. Then, the solvent was removed by using an evaporator, the residue was distilled under reduced pressure (about 1 mm Hg) by using a distiller, the distillate was dissolved with a small quantity of ethyl acetate and transferred into a 200 ml Erlenmeyer flask and then, about 150 ml of hexane was added thereinto, thereby crystals of 3-methyl-2-oxoindoline were deposited. After filtration, the synthesized crystals were washed by using hexane and dried. The synthesized crystals of 3-methyl-2-oxoindoline weighed 4.45 g (yield of 49.6%). (The structure of 3-methyl-2-oxoindoline was confirmed by coincidence in its Rf-value in TLC (Thin Layer Chromatography) with that of a standard reference material.)

Comparative Example 2 (Synthesis on a Condition of Less Using Quantity of Calcium Oxide than that of Example 1)

Similarly to Example 1, a reaction between propionylphenylhydrazide (25.0 g, 0.152 mol) and calcium oxide (5.0 g, 0.089 mol), in which a relative using quantity of calcium oxide was reduced, was advanced until the end of the ammonia gas generation, thereby 7.42 g (yield of 33.2%) of 3-methyl-2-oxoindoline crystal was synthesized after the refining processes mentioned above. (The structure of 3-methyl-2-oxoindoline was confirmed by coincidence in its Rf-value in TLC with that of a standard reference material.)

Comparative Example 3 (Synthesis on a Condition of Less Using Quantity of Calcium Oxide Similarly to Example 2)

Similarly to Example 2, a reaction between propionylphenylhydrazide (25.0 g, 0.152 mol) and calcium oxide (3.75 g, 0.067 mol), in which a relative using quantity of calcium oxide was further reduced, was advanced and followed by the refining, thereby 4.86 g (yield of 21.8%) of 3-methyl-2-oxoindoline crystal was synthesized. (The structure of 3-methyl-2-oxoindoline was confirmed by coincidence in its Rf-value in TLC with that of a standard reference material.)

Comparative Example 4

Similarly to Example 1, a reaction between propionylphenylhydrazide (5.0 g, 0.030 mol) and calcium oxide (5.0 g, 0.089 mol), was started gradually under mixing and heating at 200° C. to 205° C., however, the reaction could not be controlled since the reaction advanced rapidly halfway.

Comparative Example 5 (Synthesis on the Basis of the Conventional Process (C))

In an inert gas (Ar gas) atmosphere, a reaction between propionylphenylhydrazide (25.0 g, 0.152 mol) and calcium hydride (10.6 g, 0.251 mol) was advanced with mixing, agitating and raising temperature up to 195° C.–215° C., then ammonia gas was generated due to a rapid reaction. The reaction was completed by raising temperature up to 230° C. finally. After the end of ammonia gas generation, the reaction system was cooled down to room temperature, then methanol-water solution (ratio 2:5) (55 ml) was gradually dropped thereinto. At this time, the reaction advanced rapidly with generating hydrogen gas. Then, ethyl acetate (100 ml) was added therein and water (40 ml) was added. After the generation of hydrogen ceased, the system was neutralized with concentrated hydrochloric acid (60 ml). Then, the system was left for a night so as to decompose the unreacted solid calcium hydride completely. The separated organic layer was washed twice using water. Then, the system was dried using anhydrous magnesium sulfate followed by separation by filtration. Then, the solvent was removed, the residue was distillated under reduced pressure (about 1 mmHg) by using a distiller, the distillate was refined similarly to Comparative Example 1, thereby 11.71 g (yield of 52.8%) of 3-methyl-2-oxoindoline crystal was synthesized. (The structure of 3-methyl-2-2-oxoindoline was confirmed by coincidence in its Rf-value in TLC with that of a standard reference material.)

EXAMPLE 1

In an inert gas (Ar gas) atmosphere, tetralin (boiling point 207° C., 100 ml) was added to propionylphenylhydrazide (25.0 g, 0.152 mol) and commercially available calcium oxide powder (15.0 g, 0.267 mol), then the system was gradually heated under agitation. The reaction started at about 190° C., the system was agitated for 1.5 hours with keeping temperature at 190–200° C., then the temperature was raised up to 220° C. finally and held for 1.5 hours to advance the reaction. At that time, no violent reaction took place, therefore the reaction was well controlled. Then, the system was cooled down to room temperature, water (50 ml) was added thereinto under cooling with ice, ethyl acetate (200 ml) was added and then, concentrated hydrochloric acid (60 ml) was added gradually therein so as to neutralize the system. After the end of dissolution of the solid component, the separated organic layer was washed twice using water. The system was dried using anhydrous magnesium sulfate and separated by filtration, then the solvent was removed. The residue was distillated under reduced pressure (about 1 mm Hg, boiling point 38–45° C.) so as to recover the tetralin. The distillate was dissolved with a small quantity of ethyl acetate, then hexane (100 ml) was added thereinto, thereby crystals of 3-methyl-2-oxoindoline were deposited. After filtration, the synthesized crystals were washed by using hexane and dried. The synthesized crystals of 3-methyl-2-oxoindoline weighed 17.11 g (yield of 76.5%). The structure of 3-methyl-2-oxoindoline was confirmed by TLC and a $^1$H-NMR. spectrum (solvent: deuterated chloroform (CDCl)) as shown in FIG. 1.

EXAMPLES 2 to 7

Similarly to Example 1, syntheses of 3-methyl-2-oxoindoline were carried out with changing quantity of calcium oxide and tetralin. The: formulation of the materials and the results of the syntheses are shown in Table 1, in which (1) means propionylphenylhydrazide defined by chemical formula (1) and (2) means 3-methyl-2-oxoindoline defined by chemical formula (2). The structure of 3-methyl-2-oxoindoline was confirmed by coincidence in its Rf-value in TLC with that of a standard reference material.

TABLE 1

| Example | (1) g, mol | CaO g, mol | Tetlalin (ml) | Reaction Temp. (° C.) | Reaction Time (hr) | Yield of (2) (g) | Yield (%) |
| --- | --- | --- | --- | --- | --- | --- | --- |
| 2 | 25.0, 0.152 | 5.0, 0.089 | 50 | 200–230 | 3 | 10.13 | 45.3 |

TABLE 1-continued

| Example | (1) g, mol | CaO g, mol | Tetlalin (ml) | Reaction Temp. (° C.) | Reaction Time (hr) | Yield of (2) (g) | Yield (%) |
| --- | --- | --- | --- | --- | --- | --- | --- |
| 3 | 25.0, 0.152 | 5.0, 0.089 | 100 | 200–220 | 3 | 10.53 | 47.1 |
| 4 | 25.0, 0.152 | 7.5, 0.134 | 100 | 200–220 | 3 | 13.34 | 59.7 |
| 5 | 25.0, 0.152 | 10.0, 0.178 | 100 | 200–225 | 3 | 16.06 | 71.9 |
| 6 | 25.0, 0.152 | 20.5, 0.365 | 100 | 200–230 | 3 | 17.60 | 78.8 |
| 7 | 25.0, 0.152 | 15.0, 0.267 | 150 | 200–230 | 3 | 17.49 | 78.3 |

EXAMPLE 8

In an inert gas (Ar gas) atmosphere, similarly to Example 1, except that diisopropyl benzene (boiling point: 203–210° C., 100 ml) was used instead of tetralin, synthesis of 3-methyl-2-oxoindoline was carried out. As a result, 15.03 g (yield: 67.2%) of 3-methyl-2-oxoindoline crystals was synthesized. The structure of 3-methyl-2-oxoindoline was confirmed by coincidence in its Rf-value in TLC with that of a standard reference material.

EXAMPLE 9

In an inert gas (Ar gas) atmosphere, similarly to Example 1, except that 1,5,9-cyclododecatriene (boiling point: 237–238° C., 50 ml) was used instead of tetralin, a reaction between propionylphenylhydrazide (12.5 g, 0.076 mol) and calcium oxide (7.5 g, 0.134 mol) was advanced at 190–220° C. for 3 hours. Then, the system was cooled down to room temperature, water (30 ml) was added therein, ethyl acetate (100 ml) was added and then, concentrated hydrochloric acid (30 ml) was added therein so as to neutralize the system, then the same processes as those of Example 1 were carried out. As a result, 8.38 g (yield: 75.0%) of 3-methyl-2-oxoindoline crystals was synthesized. The structure of 3-methyl-2-oxoindoline was confirmed by coincidence in its Rf-value in TLC with that of a standard reference material.

EXAMPLES 10 to 20

Similarly to Example 9, except that various organic solvents having high boiling point were used instead of 1,5,9-cyclododecatriene, 3-methyl-2-oxoindoline was synthesized. Formulations of the materials, conditions of the reaction and yields of the syntheses are shown in Tables 2 and 3, in which (1) means propionylphenylhydrazide defined by chemical formula (1) and (2) means 3-methyl-2-oxoindoline defined by chemical formula (2). The structure of 3-methyl-2-oxoindoline was. confirmed by coincidence in its Rf-value in TLC with that of a standard reference material.

TABLE 2

| Example | Solvent | b.p. (° C.) | (1) g, mol | CaO g, mol | Reaction Temp. (° C.) | Reaction Time (hr) | Yield of (2) (g) | Yield (%) |
|---|---|---|---|---|---|---|---|---|
| 10 | diphenyl ether (50 g) | 259 | 12.5, 0.076 | 7.5, 0.134 | 200–230 | 3 | 8.09 | 72.4 |
| 11 | diethylene glycol dibutyl ether (50 ml) | 256 | 12.5, 0.076 | 7.5, 0.134 | 185–220 | 3 | 8.16 | 73.0 |
| 12 | butylphenyl ether (50 ml) | 210.3 | 12.5, 0.076 | 7.5, 0.134 | 200–230 | 3 | 8.20 | 73.4 |
| 13 | hexyl ether (50 ml) | 228–229 | 12.5, 0.076 | 7.5, 0.134 | 190–230 | 3 | 8.04 | 72.0 |
| 14 | tri-n-butyl amine (50 ml) | 216 | 12.5, 0.076 | 7.5, 0.134 | 200–230 | 3 | 6.64 | 59.4 |
| 15 | diethyl-aniline (50 ml) | 217 | 12.5, 0.076 | 7.5, 0.134 | 190–220 | 3 | 8.56 | 76.6 |

TABLE 3

| Example | Solvent | b.p. (° C.) | (1) g, mol | CaO g, mol | Reaction Temp. (° C.) | Reaction Time (hr) | Yield of (2) (g) | Yield (%) |
|---|---|---|---|---|---|---|---|---|
| 16 | ethylaniline (50 ml) | 205 | 12.5, 0.076 | 7.5, 0.134 | 190–220 | 3 | 8.00 | 71.6 |
| 17 | 1,8-diaza-bicyclo[5,4,0]-7-undecene (50 g) | 80–83/ 0.6 mm Hg | 12.5, 0.076 | 7.5, 0.134 | 215–245 | 3.5 | 6.74 | 60.3 |
| 18 | quinoline (50 g) | 113–114/ 17 mm Hg | 12.5, 0.076 | 7.5, 0.134 | 195–225 | 2.5 | 7.41 | 66.3 |
| 19 | 2,4-xylidine (50 ml) | 218 | 12.5, 0.076 | 7.5, 0.134 | 200–220 | 2 | 7.46 | 66.8 |
| 20 | 1,2,4-trichloro-benzene (50 g) | 214 | 12.5, 0.076 | 7.5, 0.134 | 200–225 | 2 | 7.12 | 63.7 |

EXAMPLE 21

A mixture of propionylphenylhydrazide (25.0 g, 0.152 mol), calcium hydride (5.5 g, 0.130 mol) and tetralin (50 ml) was heated at 190–210° C., and kept heated (for about 3 hours) until ammonia gas generation ceased. Then, the system was cooled down to room temperature and methanol-water solution (ratio 2:5) (30 ml) was gradually dropped thereinto. At this time, the reaction advanced rapidly with generating hydrogen gas. Then, ethyl acetate (100 ml) was added therein and water (30 ml) was added. After the generation of hydrogen ceased, the system was neutralized with concentrated hydrochloric acid (30 ml). Then, the system was left for a night so as to decompose the unreacted solid calcium hydride completely. The system was separated and the separated organic layer was washed twice using water. Then, the system was dried using anhydrous magnesium sulfate followed by separation by filtration. Then, the solvent was removed and the tetralin was recovered from the residue by distillation under reduced pressure. Then, the residue was distillated under reduced pressure (about 1 mm Hg) by using a distiller. The distillate was dissolved with a small quantity of ethyl acetate and transferred into an Erlenmeyer flask and then, hexane (100 ml) was added thereinto, thereby crystals of 3-methyl-2-oxoindoline were deposited. After cooling with ice and filtration, the synthesized crystals were washed by using hexane followed by drying. The synthesized crystals of 3-methyl-2-oxoindoline weighed 14.0 g (yield of 62.6%). The structure of 3-methyl-2-oxoindoline was confirmed by coincidence in its Rf-value in TLC with that of a standard reference material.

EXAMPLE 22

A mixture of propionylphenylhydrazide (5.0 g, 0.030 mol), calcium carbide (3.0 g, 0.058 mol) and tetralin (20 ml) was heated under agitation. The reaction started at about 210° C. and violently advanced at 220° C. with generating ammonia gas. The system was heated up to 235° C. finally so as to complete the reaction. Then, the system was cooled down to room temperature and water was gradually added therein so as to decompose the calcium carbide. Then, ethyl acetate (50 ml) was added therein and the system was neutralized by adding 20%-hydrochloric acid solution (50 ml). Then, the system was left for a night. The system was separated and the separated organic layer was washed twice using water. Then, the system was dried using anhydrous magnesium sulfate. A small quantity of cerite was added therein and a filtration was done. Then, the ethyl acetate was removed from the filtrate. The tetralin was recovered by distillation under reduced pressure. Then, the residue was distillated under reduced pressure by using a distiller. The distillate was dissolved with a small quantity of ethyl acetate and transferred into an Erlenmeyer flask and then, hexane (30 ml) was added thereinto, thereby crystals of 3-methyl-2-oxoindoline were deposited. After cooling with ice and filtration, the synthesized crystals were washed by using hexane followed by drying. The synthesized crystals of 3-methyl-2-oxoindoline weighed 2.72 g (yield of 61.7%). The structure of 3-methyl-2-oxoindoline was confirmed by coincidence in its Rf-value in TLC with that of a standard reference material.

EFFECTS OF THE INVENTION

A process for producing 3-methyl-2-oxoindoline according to the present invention does not require expensive calcium hydride and enables a marked reduction in using quantity of calcium oxide in comparison with the quantity conventionally used, a high yield, a sharp cut of cost, and simplification of after treatment since the refining or after treatment becomes very easy to be implemented.

Therefore, the process for producing 3-methyl-2-oxoindoline according to the present invention is highly efficient and excellent.

Figure 1:
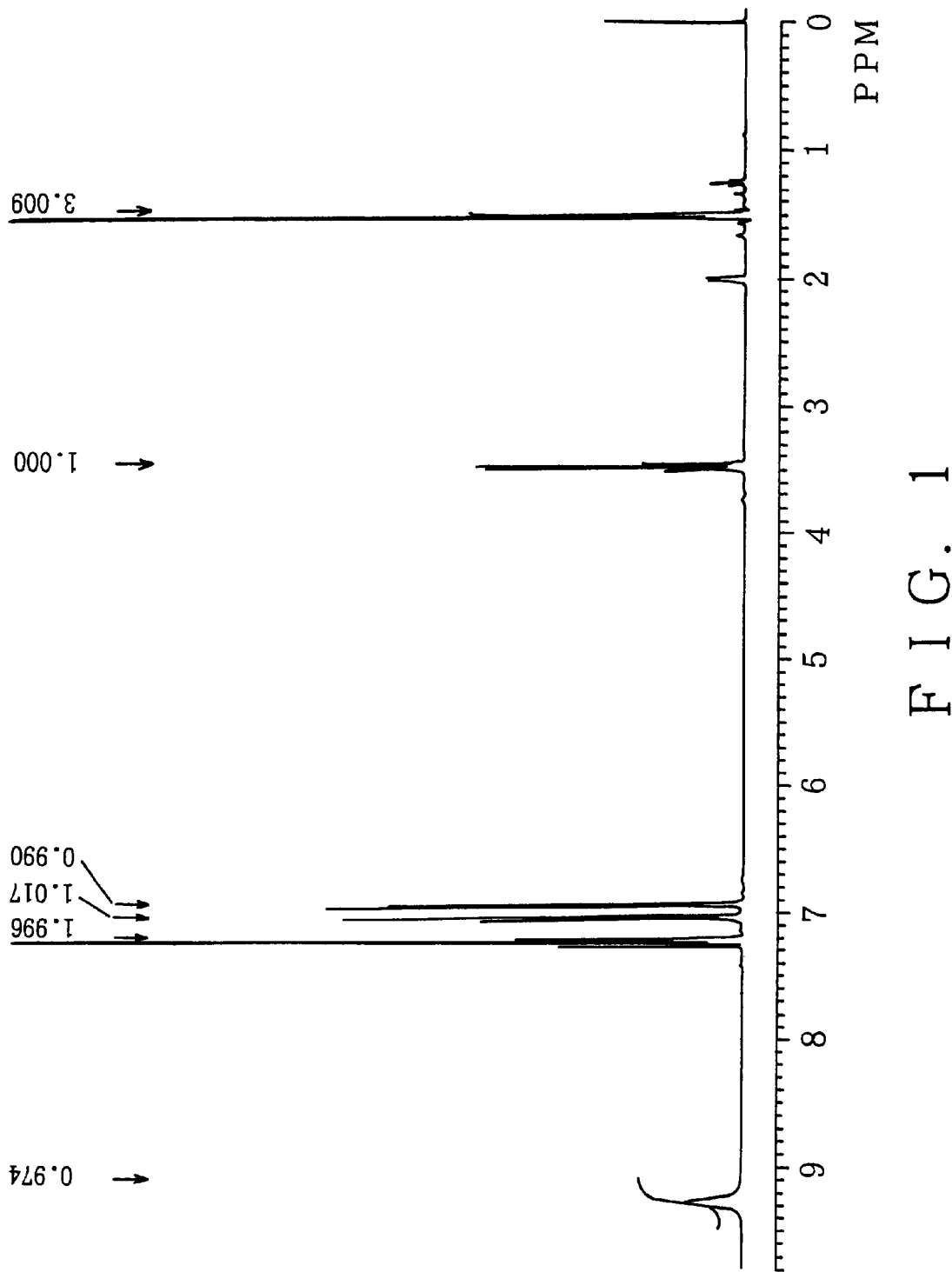
FIG. 1 is a $^1$H-NMR (Nuclear Magnetic Resonance) spectrum of 3-methyl-2-oxoindoline synthesized in the Example of the present invention.

What is claimed is:

1. A process for producing 3-methyl-2-oxoindoline as defined by the following chemical formula (2), comprising heating of propionylphenylhydrazide as defined by the following chemical formula (1) in the presence of calcium oxide, wherein an organic solvent, which has a boiling point of 180° C. or the higher and is thermally stable at temperatures from 180° C. to 300° C. in the presence of calcium oxide, is employed by at least an amount of equal weight to that of the propionylphenylhydrazide;

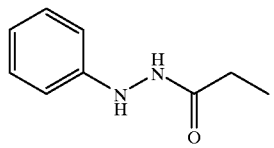

(1)

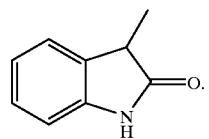

(2)

2. The process for producing 3-methyl-2-oxoindoline according to claim 1, wherein the organic solvent is at least one member selected from the group consisting of tetrahydronaphthalin, diisopropylbenzene, diethylaniline, ethylaniline, diethylene glycol dibutyl ether, diphenyl ether, butylphenyl ether, hexyl ether, and 1,5,9-cyclododecatriene.

* * * * *